US011123121B2

(12) United States Patent
Miller

(10) Patent No.: US 11,123,121 B2
(45) Date of Patent: Sep. 21, 2021

(54) CORACOCLAVICULAR FIXATION DEVICE AND RELATED METHOD THEREOF

(71) Applicant: University of Virginia Patent Foundation, Charlottesville, VA (US)

(72) Inventor: Mark D. Miller, Crozet, VA (US)

(73) Assignee: University of Virginia Patent Foundation, Charlottesville, VA (US)

( * ) Notice: Subject to any disclaimer, the term of this patent is extended or adjusted under 35 U.S.C. 154(b) by 66 days.

(21) Appl. No.: 16/099,250

(22) PCT Filed: May 10, 2017

(86) PCT No.: PCT/US2017/031929
§ 371 (c)(1),
(2) Date: Nov. 6, 2018

(87) PCT Pub. No.: WO2017/196959
PCT Pub. Date: Nov. 16, 2017

(65) Prior Publication Data
US 2019/0142486 A1 May 16, 2019

Related U.S. Application Data

(60) Provisional application No. 62/335,838, filed on May 13, 2016.

(51) Int. Cl.
*A61B 17/84* (2006.01)
*A61B 17/82* (2006.01)
*A61B 17/88* (2006.01)

(52) U.S. Cl.
CPC ............ *A61B 17/842* (2013.01); *A61B 17/82* (2013.01); *A61B 17/8869* (2013.01)

(58) Field of Classification Search
CPC ..... A61B 17/842; A61B 17/82; A61B 17/823; A61B 17/8869
See application file for complete search history.

(56) References Cited

U.S. PATENT DOCUMENTS

| | | | |
|---|---|---|---|
| 4,644,940 A * | 2/1987 | Nakamura | A61F 5/019 128/882 |
| 5,409,490 A | 4/1995 | Ethridge | |
| 5,645,588 A | 7/1997 | Graf et al. | |

(Continued)

FOREIGN PATENT DOCUMENTS

WO    WO 2016/154550 A1    9/2016

OTHER PUBLICATIONS

Baldwin, et al., "Luggage Tag Technique of Anatomic Fixation of Displaced Acromioclavicular Joint Separations", Clinical Orthopaedics and Related Research, 2010, pp. 259-265, vol. 468, No. 1.

(Continued)

*Primary Examiner* — Kevin T Truong
*Assistant Examiner* — Tracy L Kamikawa
(74) *Attorney, Agent, or Firm* — Robert J. Decker

(57) ABSTRACT

An adjustable and self-locking fixation device for fixedly securing two structures wherein the device comprises two spans and a receiving aperture configured to receive the spans and form a closed loop around a first structure. The two spans are further configured to secure and lock onto each other so as to form a second closed loop around the two structures and secure the two structures in a tensioned state.

13 Claims, 4 Drawing Sheets

(56) References Cited

U.S. PATENT DOCUMENTS

| | | | |
|---|---|---|---|
| 5,766,218 | A | 6/1998 | Arnott |
| 5,964,765 | A | 10/1999 | Fenton, Jr. et al. |
| 8,162,997 | B2 | 4/2012 | Struhl |
| 8,512,376 | B2 | 8/2013 | Thornes |
| 8,740,913 | B2 | 6/2014 | Schneider |
| 8,936,621 | B2* | 1/2015 | Denham ............... A61F 2/0811 606/232 |
| 9,332,979 | B2 | 5/2016 | Sullivan et al. |
| 9,387,011 | B2 | 7/2016 | Chudik |
| 9,468,433 | B2 | 10/2016 | Denham et al. |
| 2007/0016208 | A1 | 1/2007 | Thornes |
| 2007/0270804 | A1 | 11/2007 | Chudik |
| 2008/0071299 | A1* | 3/2008 | Allinniemi ............ A61B 17/82 606/151 |
| 2009/0182335 | A1 | 7/2009 | Struhl |
| 2012/0041441 | A1* | 2/2012 | Bernstein ............ A61B 17/823 606/74 |
| 2012/0053630 | A1 | 3/2012 | Denham et al. |
| 2012/0116402 | A1 | 5/2012 | Schneider |
| 2012/0123474 | A1* | 5/2012 | Zajac ................... A61B 17/842 606/232 |
| 2013/0023929 | A1 | 1/2013 | Sullivan et al. |
| 2017/0265917 | A1* | 9/2017 | Dreyfuss .......... A61B 17/06166 |

OTHER PUBLICATIONS

Milewski et al., "Complications Related to Anatomic Reconstruction of the Coracoclavicular Ligaments", The American Journal Sports Medicine, 2012, pp. 1628-1634, vol. 40, No. 7.

Shewy, et al., "Suture Repair Using Loop Technique in Cases of Acute Complete Acrmioclavicular Joint Dislocation", Journal of Ortopaed Traumatol, 2011, pp. 29-35, vol. 12.

Turman et al, "Clavicular Fractures Following Coracoclavicular Ligament Reconstruction with Tendon Graft", The Journal of Bone & Joint Surgery, Jun. 2010, pp. 1526-1532, vol. 92-A, No. 6.

* cited by examiner

CORACOCLAVICULAR FIXATION DEVICE AND RELATED METHOD THEREOF

RELATED APPLICATIONS

The present application is a national stage filing of International Application No. PCT/US2017/031929, filed May 10, 2017, which claims benefit of priority under 35 U.S.C § 119 (e) from U.S. Provisional Application Ser. No. 62/335,838, filed May 13, 2016, entitled "Coracoclavicular Fixation Device (C-C Link)"; the disclosures of which are hereby incorporated by reference herein in their entirety.

FIELD OF INVENTION

The present invention has a broad application in the field of orthopedic surgery. Certain embodiments of the present invention may be utilized in any setting where the separation between two anatomic structures must be reduced and the two structures stabilized in order to promote healing. More particularly, specific applications of certain embodiments of the present invention relate to the stabilization and repair of acromioclavicular joints following severe injury.

BACKGROUND

Joint dislocations are a common injury, and injuries to the acromioclavicular (AC) joint represent a substantial portion of such injuries affecting the shoulder girdle (See Milewski M D, Tompkins M A, Guigale J M, Carson E W, Miller M D, Diduch D R. Complications Related to Anatomic Reconstruction of the Coracoclavicular Ligaments", Am. J. Sports Med., 2012; 40: 1628-1634; herein after "Milewski et al."). Such injuries to the AC joint may involve an upward displacement of the clavicle relative to the acromion and coracoid. These injuries are also associated with damage to the acromioclavicular (AC) ligaments and coracoclavicular (CC) ligaments. Such injuries are classified into one of six categories according to increasing severity (See Mohamed Taha El Shewy, et al., "Suture Repair Using Loop Technique in Cases of Acute Complete Acrmioclavicular Joint Dislocation", Journal of Ortopaed Traumatol (2011), 12:29-35; herein after "Shewy et al."). In other words, Type I sprains are the least severe and Type VI are the most severe. While most AC joint injuries may be treated without surgery, more severe dislocations may require surgical treatment in order to allow the damaged anatomical structures to properly heal. Surgery is recommended for certain Type III injuries, and typically required for most Type IV, V, and VI injuries to properly heal (See Shewy et al.) During surgery, the separation between the displaced clavicle and the acromion and coracoid bones is reduced and the joint is stabilized. More than sixty techniques have been described to treat such injuries, and the ideal technique remains in dispute (See Turman K A, Miller C D, Miller M D, "Clavicular fractures following coracoclavicular ligament reconstruction with tendon graft: a report of three cases", J Bone Joint Surg. 2010; 92(6):1526-32; herein after "Turman et al.").

Known techniques for the surgical repair include the Weaver-Dunn coracoacromial ligament transfer and modified Weaver-Dunn techniques involving supplemental fixation of the coracoid and clavicle. These techniques were previously among the most commonly utilized to treat acute and chronic injuries (See Turman et al.). In some of these techniques, bone tunnels are drilled into the coracoid process and clavicle in order to accommodate a tendon graft that is subsequently fixed to the structures using a bone screw. Though these techniques restore the integrity of the CC ligaments, they nonetheless possess significant limitations (See Baldwin, K., et al., "Luggage Tag Technique of Anatomic Fixation of Displaced Acromioclavicular Joint Separations", Clinical Orthopaedics and Related Research (2010), 468: 259-265; herein after "Baldwin et al."). For instance, drilling a hole in the coracoid process has been associated with an increased incidence of coracoid fractures (See Baldwin et al.). Some of these techniques have also been associated with incomplete reduction of the AC joint, reducing overall efficacy of the treatment (See Turman et al). Newer techniques utilizing various alternative tendon grafts have also been associated with limitations and complications, such as clavicular fractures from the use of bone tunnels (See Turman et al.). Minimally invasive and arthroscopic techniques are technically demanding and the long-term efficacy of such techniques is not yet known (See Turman et al.).

Partly because of the increased incidence of coracoid fractures associated with the coracoid bone tunnels utilized in modified Weaver-Dunn techniques and other surgical methods, certain techniques have been developed in which a prosthetic device is looped around the coracoid, and such a technique still requires the use of bone tunnels to secure a prosthetic device or tendon graft to the clavicle whereby it has been associated with clavicular fractures, hardware failure, and re-injury (See Turman et al.). Moreover, currently available prosthetic devices are currently configured to operate using more invasive techniques, such as bone tunneling and screw fixation (See: U.S. Pat. No. 8,162,997 B2, Struhl, S., "Device for Treatment of Acromioclavicular Joint Dislocations", Apr. 24, 2012; U.S. Pat. No. 8,512,376 B2, Thornes, B., "Method and Apparatus for Internal Fixation of an Acromiclavicular Joint Dislocation of the Shoulder", Aug. 20, 2013; U.S. Pat. No. 9,332,979 B2, Sullivan, et al., "Tensionable Knotless Acromiclavicular Repairs and Constructs", May 10, 2016; and U.S. Pat. No. 9,387,011 B2, Chudik, S., "Acromioclavicular Joint Repair System," Jul. 12, 2016.). Other devices currently being used with the coracoid looping technique are limited by their difficulty of use, including the difficulty of adjusting the device and the necessity of additional tools in securing said device (See International Patent Application Publication No. WO 2016/154550 A1, Golden, et al., "Joint Repair System", Sep. 29, 2016; herein after "Golden et al.").

None of the patents and patent applications described above provides the important advantages of providing a self-locking and adjustable device that secures and stabilizes two anatomical structures, such as a coracoid and clavicle, without the use of additional tools to lock the device or bone tunneling techniques to secure the device.

SUMMARY OF EXEMPLARY EMBODIMENTS OF THE INVENTION

An aspect of an embodiment of present invention provides, among other things, an improved, adjustable, and self-locking fixation device (and related method) configured to secure two anatomic structures, such as a coracoid and a clavicle.

An aspect of an embodiment of the present invention provides, among other elements, an adjustable and self-locking device for the secure fixation of two anatomic structures. An aspect of an embodiment of the present invention device and related method provides, but is not limited thereto, secure fixation of the clavicle and the coracoid in a tensioned state for the treatment of acromioclavicular injuries, such as advanced grade sprains and separations.

An adjustable and self-locking fixation device for fixedly securing two structures wherein the device may comprise two spans (or more) and a receiving aperture (or greater than one receiving aperture) configured to receive the spans and form a closed loop around a first structure. The two spans may be further configured to secure and lock onto each other so as to form a second closed loop around the two structures and secure the two structures in a tensioned state. It should be understood that more than two spans and receiving apertures may be implemented as part of the fixation device so as to form additional corresponding first and second loops, and interact with a variety of types of anatomical structures as well as number of anatomical structures.

In some non-limiting embodiments, the fixation device may comprise a first span, wherein the first span comprises at least one securement means on a proximal portion of the first span. Further, the fixation device may comprise a second span in communication with the first span. In some non-limiting embodiments, attachment means may be disposed on a surface of the second span.

The securement means on the first span may be, but are not limited to, at least one aperture, recess, groove, socket, notch, hole, orifice, slit, slot, duct, cavity, or other suitable equivalents thereof. The attachment means on the second span may be, but are not limited to, a protrusion, tab, clamp, hook, lock, rivet, or other suitable form or structure for engaging and securedly attaching to the securement means as described.

Further, in some non-limiting embodiments, the first span may comprise a receiving aperture that is configured to receive the first and second span as they are passed through the receiving aperture. In some non-limiting embodiments, the device may form a closed loop around a first anatomic structure, such as, for example, a coracoid bone of a human being. This arrangement allows for a secure attachment to, for example, the coracoid bone without having to drill through the coracoid or otherwise engage in more invasive techniques to secure the fixation device to the bone. However, this coracoid application is not necessary, and the loop formed by the receiving aperture and the first and second spans may engage any other suitable anatomic structure such as, for example, a portion of a human being's sternum, a tibia of a human being, or a fibula of a human being.

Further, in some non-limiting embodiments, the first and second span may further extend around a second anatomic structure, such as, for example, a clavicle of a human being. However, this clavicle application is not necessary, and the first and second spans may loop around any other suitable anatomic structure, such as, for example, a portion of human being's sternum, a fibula of a human being, or a tibia of a human being.

In some non-limiting embodiments, the first and second spans may be further adjusted in order to reduce the separation between two anatomic structures, such as, for example, the coracoid and clavicle of a human being. Alternatively, adjustment of two anatomic structures may be accomplished using surgical techniques that would be familiar to those of ordinary skill in the art, such as, for example, the reduction techniques described by Shewy et al., Milewski et al., and Turman et al.

In some non-limiting embodiments, after the appropriate adjustment is made to the orientation of the two anatomic structures, such as, for example, the separation between a coracoid and a clavicle, a user may secure the first span directly to the second span, or vice versa, in order to form a closed loop around both the second anatomic structure and first anatomic structure such that both anatomic structures will be secured in an appropriately tensioned state. It should be appreciated that the present invention allows for an easy adjustment in this regard and does not require more invasive techniques in order to secure the two anatomic structures in a tensioned state, such as, for example, the use of bone tunneling techniques as herein described. Moreover, it should be appreciated that no additional tools, other than those used in conventional surgical techniques known to those of ordinary skill in the art, are needed to secure the first span to the second span.

In some non-limiting embodiments, this securement and fixation is accomplished by engaging at least one securement means on the first span with at least one attachment means on the second span. For example, an aperture on the first span may engage a protrusion on the second span. However, this is not necessary, and the first span may be attached to the second span using any appropriate means. As additional non-limiting examples, a recess, groove, socket notch, hole, orifice, slit, slot, duct, cavity, or other suitable structure on the first span may snap, engage, attach, or lock on to a protrusion, tab, clamp, hook, lock, rivet, or other suitable form or structure on the second span to engage and fix the first and second spans together. Alternatively, the attachment means may be disposed on the first span, while the securement means may be disposed on the second span.

In some embodiments of the present invention, the fixation device as herein described may be packaged with a passing device configured to advance the fixation device so as to traverse the fixation device adjacent a first anatomic structure, such as, for example, a coracoid.

In some non-limiting embodiments, a method for stabilizing and securing two anatomic structures, such as a coracoid and a clavicle, is disclosed. This method may comprise 1) advancing a fixation device so as to traverse the fixation device adjacent to a first anatomic structure, such as a coracoid; 2) passing a first span and a second span of the fixation device through a receiving aperture of the device in order to form a first closed loop around the first anatomic structure; 3) passing the first span and the second span of the fixation device so as to collectively extend around a second anatomic structure, such as a clavicle; 4) reducing the separation between the first anatomic structure and the second anatomic structure; 5) overlapping the first span and the second span to an appropriate degree such that the first structure and the second structure will be secured in a tensioned state; and 6) affixing an attachment means, such as a protrusion, disposed on the second span of the fixation device to a securement means, such as an aperture, disposed on the first span of the fixation device in order to form a second closed loop around the first anatomic structure and the second anatomic structure in a tensioned state. The fixation device utilized in the foregoing method may be the fixation device as herein described.

In some non-limiting embodiments, the method for stabilizing and securing two anatomic structures may further comprise inserting a passing device into a space adjacent to a first anatomic structure so as to transverse the first anatomic structure, and utilizing the passing device to advance a fixation device, such as the fixation device as herein described, so as to traverse the fixation device adjacent to the first anatomic structure.

It should be appreciated that no additional tools, other than those used in conventional surgical techniques known to those of ordinary skill in the art, are needed to secure the first span to the second span. It should also be appreciated that the device locks on to itself such that no additional hardware, such as, for example, bone screws, must be introduced in to the subject's anatomy in order to secure the two anatomic structures in a tensioned state. Therefore, the present invention can be more easily adjusted and utilized than other fixation devices, prosthetic devices, and sutures in the prior art. Additionally, this device provides the important advantage of securing two anatomic structures without the use of more invasive techniques, such as bone tunneling, and thus mitigates risks such as bone fracture, reduction of separation, and re-injury as observed with the use of other techniques. Moreover, no additional hardware or mechanisms are required for re-sizing or unlocking the affixed fixation device.

The invention itself, together with further objects and attendant advantages, will best be understood by reference to the following detailed description, taken in conjunction with the accompanying drawings.

DETAILED DESCRIPTION OF EXEMPLARY EMBODIMENTS OF THE INVENTION

Turning now to the drawings, the subject invention, as shown in FIGS. 1-6 includes a fixation device 11 for the secure fixation and stabilization of two anatomic structures, such as, for example, a coracoid 27 and clavicle 25.

The present invention has a broad application in the field of orthopedic surgery. Exemplary applications of the technology herein disclosed include stabilization and repair of advanced grade acromioclavicular injuries, such as sprains, or any other procedure wherein the separation between two anatomic structures must be reduced and said anatomic structures must be stabilized in a fixed position. Additional non-limiting examples include the reduction and stabilization of the tibia and fibula syndesmosis and split sternum repair.

Figure 1:
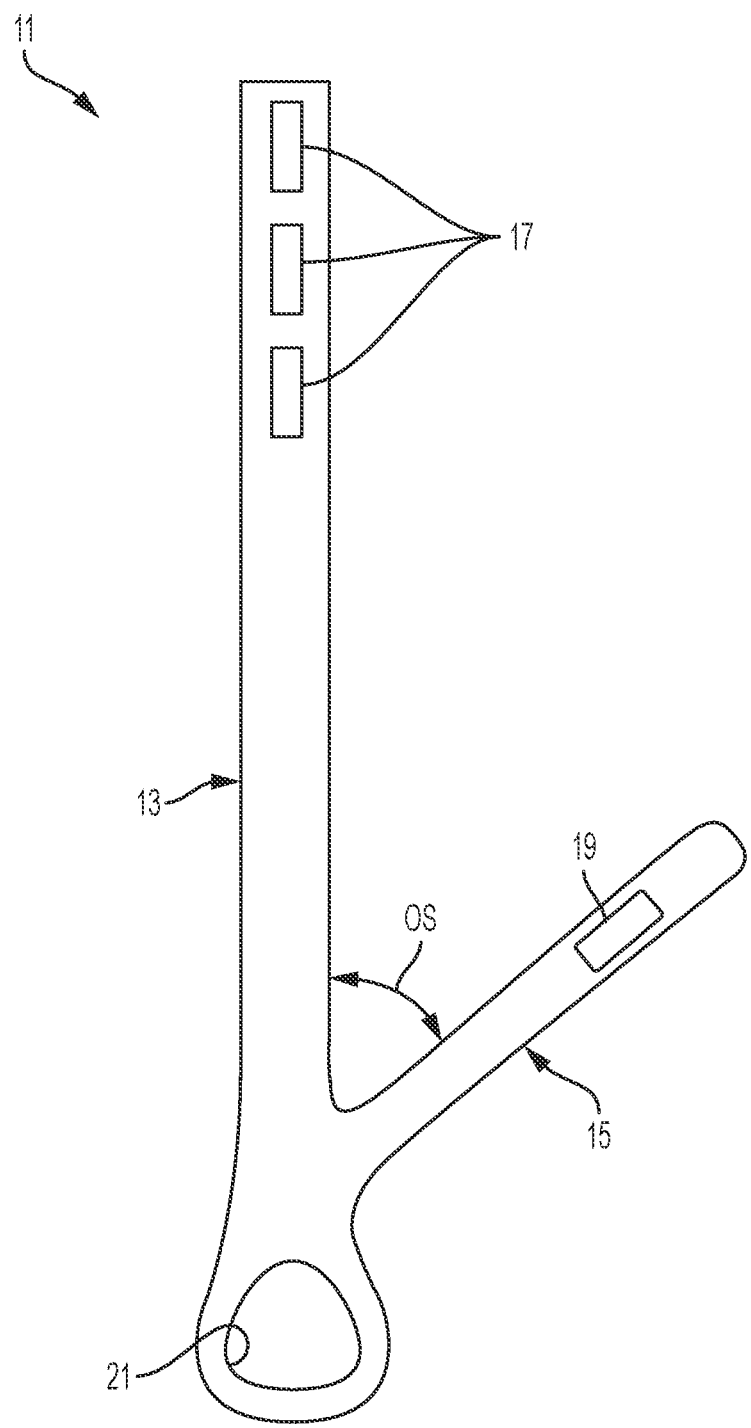
FIG. 1 is a plan view of a fixation device in accordance with an embodiment.

FIG. 1 illustrates an exemplary and non-limiting embodiment of the present invention. A fixation device 11 comprises a first span 13 and a second span 15 in communication with the first span 13 whereby the second span 15 is offset from the first span 13 at a specified offset angle (denoted as OS) such as a preformed non-zero angle.

The first span 13 further comprises at least one securement means 17 on a proximal portion of the first span 13. The first span 13 further comprises a receiving aperture 21 on a distal portion opposite said proximal portion of the first span 13. The second span 15 further comprises at least one attachment means 19 disposed on a surface of the second span 15.

The securement means 17 may be a variety of forms and mechanisms suitable to engage, interface, lock, or attach to the attachment means 19. For example, the securement means 17 may be at least one aperture, recess, groove, socket, notch, hole, orifice, slit, slot, duct, cavity, or suitable equivalents thereof. Alternative embodiments of the present invention may include a plurality of such securement means 17 that may extend in a linear and sequential fashion away from the proximal portion of the first span 13. Providing a plurality of securement means 17 allows a user to easily adjust the size and fit of the fixation device 11 and overcomes limitations encountered in prior art devices such as the need for pre-sizing. In other words, the present invention may function as a "one-size fits all" device. However, this is not necessary, and a single securement means 17 may be utilized to secure the fixation device 11. Alternatively, the securement means 17 may be located on the second span 15. In this alternative exemplary and non-limiting embodiment, the second span 15 may comprise a plurality of securement means 17 that may extend in a linear and sequential fashion away from a proximal portion of the second span 15. Such securement means 17 may take the form of the securement means herein described, or suitable equivalents thereof.

The attachment means 19 may be a variety of forms and mechanisms suitable to be engaged by, interfaced with, locked to, or attached to the securement means 17. For example, the attachment means 19 may be at least one protrusion, tab, clamp, hook, lock, rivet, or suitable equivalents thereof disposed on a surface of the second span 15. Alternatively, the attachment means 19 may be disposed on a surface of the first span 13. In this alternative exemplary and non-limiting embodiment, such attachment means 19 may take the form of the attachment means herein described, or suitable equivalents thereof. Consequently, designating the specific spans as being either "first" or "second" may be interchanged such that the fixation device 11 would operate and function in the same fashion for either designation. To that end, the specific drawings as illustrated herein could swap the terms "first span" and "second span" without any change in operation or function to the fixation device 11.

Figure 2:
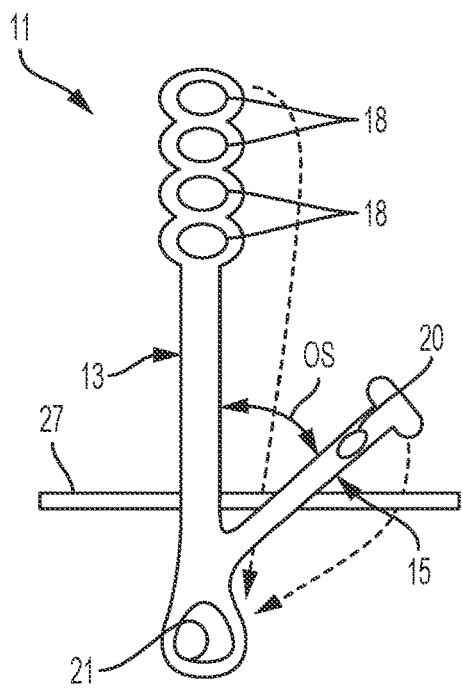
FIG. 2 is a perspective view of a fixation device with securement apertures on a first span and a protrusion disposed on a second span in accordance with an embodiment.
Figure 7:
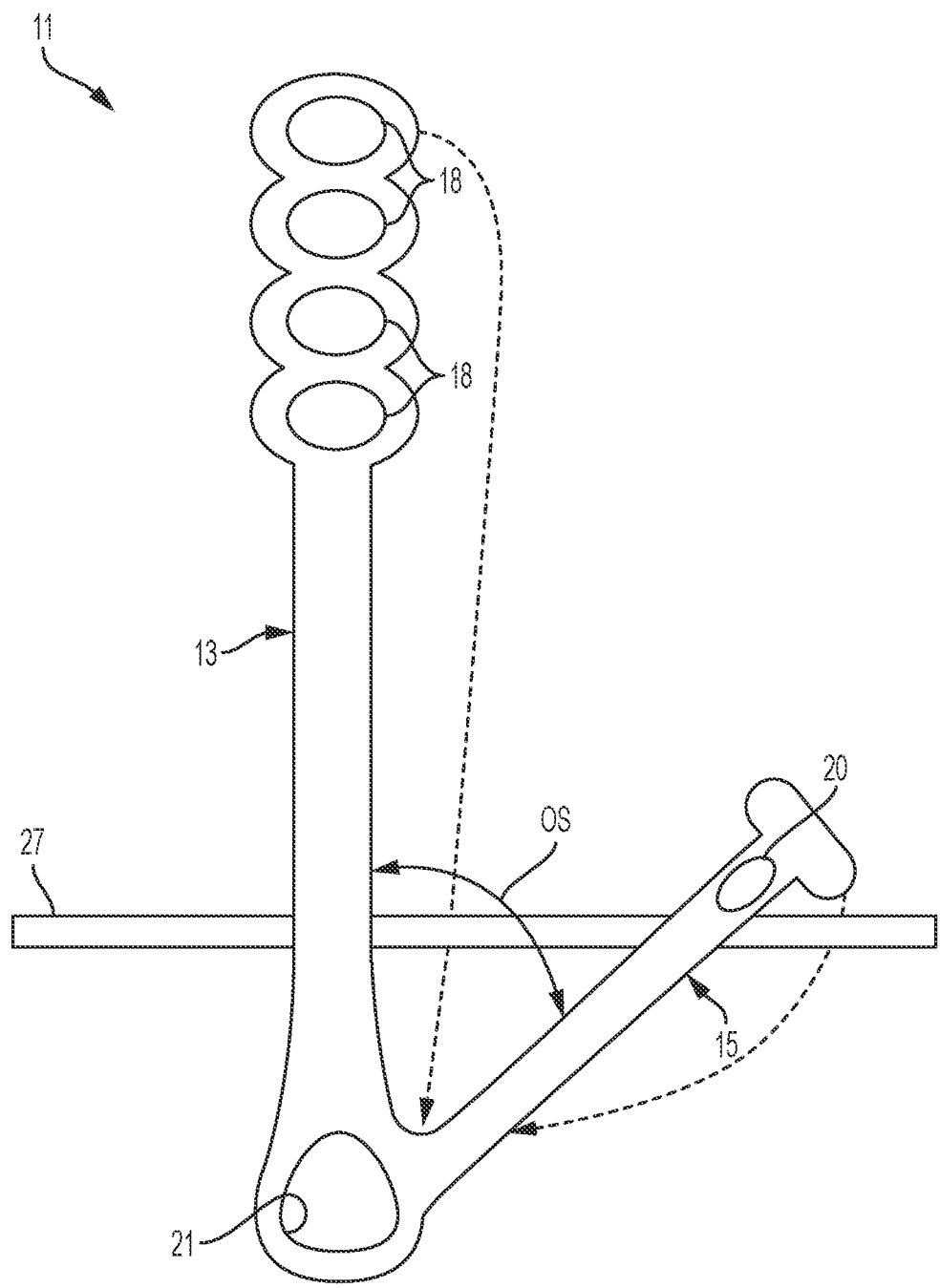
FIG. 7 is a perspective view of a fixation device, as an alternative embodiment to FIG. 2, with securement apertures on a first span and a protrusion disposed on a second span in accordance with an embodiment.

FIG. 2 illustrates an additional exemplary embodiment of the fixation device 11 of the present invention relative to a first anatomic structure, which may be the coracoid 27, for example. The securement means on the proximal portion of the first span 13 are depicted as apertures or recesses (indentations) 18 and the attachment means are depicted as a protrusion 20 on the second span 15. The second span 15 is offset from the first span 13 at a specified offset angle (denoted as OS) such as a preformed non-zero angle. Also illustrated is a receiving aperture 21 that may be substantially located on the distal end of the first span 13. Alternatively, the receiving aperture 21 may be substantially located on the second span 15 or a combination of the first span 13 and second span 15 as shown in FIG. 7.

FIG. 2 further illustrates a plurality of apertures 18 (forming the securement means) extending linearly in a sequential fashion away from the proximal portion of the first span 13. By way of example, four apertures or recesses 18 (of the securement means) are pictured. However, this precise number of apertures or recesses 18 (or other types of securement means) is not necessary and is shown as depicted for exemplary purposes only. An embodiment may provide any suitable number of apertures or recesses 18 (or other types of securement means) for inclusion so as to provide for an adjustable fit of the fixation device 11 prior to securing the two anatomic structures (e.g., bones) in a tensioned state.

Figure 3:
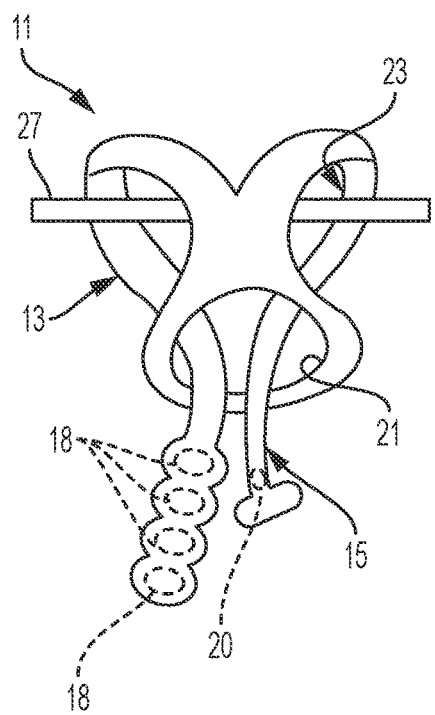
FIG. 3 is a perspective view of a fixation device in a closed loop configuration in accordance with an embodiment.

FIG. 3 further illustrates an exemplary embodiment of the fixation device 11 of the current invention in an exemplary configuration. As shown in FIG. 3, the first span 13 and second span 15 have been advanced around the same side of the first structure (for example, the coracoid 27) and then passed through the receiving aperture 21 so as to form a first closed loop 23. The first closed loop 23 as shown in FIG. 3 may engage and secure a first anatomic structure (e.g., coracoid 27) without additional hardware, so as to avoid complications as described in the prior art. This view is provided for exemplary purposes only, and the actual operation of the fixation device 11 in practice may differ from what has been described. The protrusion 20 (e.g., attachment means) as illustrated in FIG. 3 is represented by dashed lines as protrusion 20 (e.g., attachment means) and is facing on second span 15 opposite to face of illustration sheet. The securement means as illustrated in FIG. 3 are dashed lines in the event the securement means are recesses 18 (rather than apertures) facing on first span 13 opposite to face of illustration sheet. However, these orientations are depicted in for exemplary purposes only, and the orientations of the foregoing structural elements may be adjusted in order to meet the anatomic, environmental, and structural demands of particular operational requirements.

Figure 4:
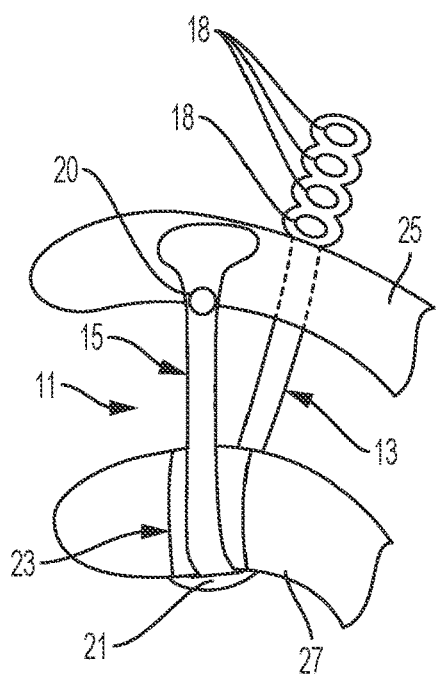
FIG. 4 is a perspective view of a fixation device in a closed loop configuration around a coracoid bone in accordance with an embodiment.

FIG. 4 further illustrates an exemplary embodiment of the fixation device 11 in a configuration that may be seen in an exemplary use of the present invention. A coracoid 27 has been secured by the first closed loop 23 (as discussed previously with FIG. 3). For instance, the first closed loop 23 may have been formed by advancing the first span 13 and second span 15 around or along the same side of the first anatomic structure (for example, the coracoid 27) and then passing the first span 13 and second span 15 through the receiving aperture 21. As illustrated, the first span 13 and second span 15 extend upward or away from the first closed loop 23.

In FIG. 4, the first span 13 is depicted as extending around the posterior portion of a clavicle 25 and the second span 15 is depicted as extending upward toward the anterior portion of the clavicle 25. However, this exact arrangement is not necessary and it should be appreciated that the first span 13 and second span 15 may extend upward or away from the first closed loop 23 from a number of acceptable orientations and approaches as they engage the clavicle 25.

Figure 5:
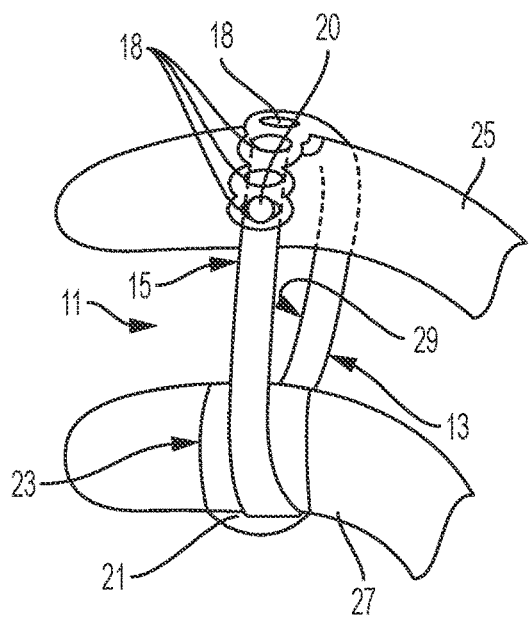
FIG. 5 is a perspective view of a fixation device in a secured closed loop configuration around a coracoid bone and clavicle in accordance with an embodiment.

FIG. 5 further illustrates an exemplary embodiment of the fixation device 11 in a configuration that may be seen in an exemplary use of the present invention, such as, for example, the treatment and repair of a severe acromioclavicular joint injury. The first closed loop 23 secures the coracoid 27, such as in the manner previously depicted in FIG. 4. In the illustrated embodiment, the first span 13 extends upward from the first closed loop 23 and extends around the posterior portion of the clavicle 25. Additionally, as depicted in FIG. 5, in the illustrated embodiment, the second span 15 extends upward from the first closed loop 23 and rests on the anterior surface of the clavicle 25. However, this exact arrangement is not necessary and it should be appreciated that the first span 13 and second span 15 may extend upward from the first closed loop 23 from a number of acceptable orientations and approaches as they engage the clavicle 25.

After a user has reduced the separation between the coracoid 27 and clavicle 25 in an effective manner (or as the user reduces the separation by adjusting the first span 13 and the second span 15), the first span 13 is attached and secured to the second span 15 in order to form a second closed loop 29 around the coracoid 27 and clavicle 25 in order to secure the two bones in a therapeutically effective tensioned state. Such attachment is accomplished by affixing the apertures or recesses 18 (as a type of securement means) located on the first span 13 to the protrusion 20 (as a type of an attachment means) located on the second span 15. In the illustrated embodiment of FIG. 5, the securement means are depicted as a series of apertures 18 extending linearly in a sequential fashion. Once the appropriate reduction of separation between the coracoid 27 and the clavicle 25 has been achieved in a therapeutically effective distance or state (or while the separation is being achieved by adjusting the overlap of the first span 13 and the second span 15, for example), a user may extend the first span 13 around the clavicle 25 and overlap the first span 13 around the second span 15 such that a closed loop 29 is formed around the coracoid 27 and clavicle 25. In FIG. 5, the second closed loop 29 is securely fixed by engaging an aperture 18 and the attachment means, which is depicted as a protrusion 20 in this exemplary and non-limiting embodiment. Thus, FIG. 5 depicts an acromioclavicular joint secured in a tensioned state after reducing the separation, sustained during an injury, of a clavicle 25 and coracoid 27 in accordance with an embodiment of the present invention.

Unlike certain devices in the prior art, such as, for example Golden et al., pertaining to an aspect of various embodiments of the present invention, no additional tools are necessary to fix the securement means (e.g., aperture or recess 18) to the attachment means 19 (e.g., protrusion 20), other than those tools conventionally utilized during surgical techniques known to those of ordinary skill in the art. Additionally, the securement means (e.g., aperture or recess 18) and the attachment means (e.g., protrusion 20) may be easily disengaged and readjusted if necessary. Thus, an aspect of various embodiments of the present invention allows for greater flexibility and ease of use than certain prior art devices allow.

Figure 6:
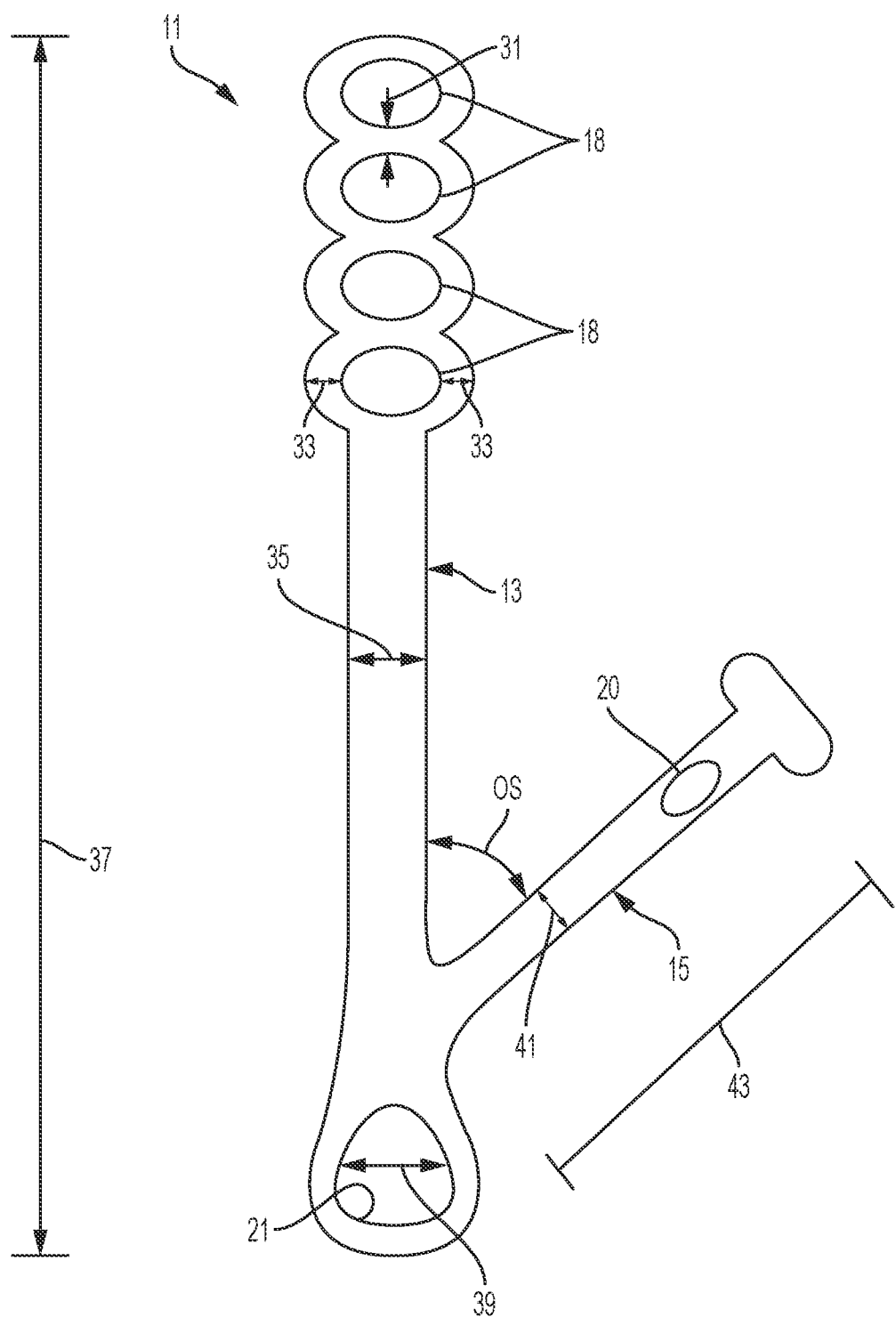
FIG. 6 is a perspective view of a fixation device illustrating exemplary dimensions in accordance with an embodiment.

FIG. 6 illustrates another exemplary and non-limiting embodiment of the fixation device 11 of the present invention, along with exemplary and non-limiting dimensions thereof. The second span 15 is offset from the first span 13 at a specified offset angle (denoted as OS) such as a preformed non-zero angle. The first span 13 is depicted as having a width of first span 35 and a length of first span 37. In certain embodiments, the width of first span 35 may be about five to about 100 millimeters and the length of first span 37 may be about six to about fourteen centimeters, with a preferred length of, for example, about eight to about twelve centimeters in certain embodiments. The width of first span 35 and a length of first span 37 may be less than or greater than as listed. In certain embodiments, the width of first span 35 may be about one to about 300 millimeters and the length of first span 37 may be about two to about fifty centimeters (or may be less than or greater than as desired or required). However, the provided dimensions for both the width of the first span 35 and the length of first span 37 are exemplary and not limiting. It should be appreciated that these dimensions may vary considerably based upon the anatomical, environmental, and structural demands and operational requirements. For example, these dimensions may vary based on an individual patient's anatomy. Moreover, these dimensions may vary depending on the targeted anatomical region. That is, when a certain embodiment of the fixation device 11 is used, for example, to stabilize the syndesmosis of the tibia and fibula, the width of first span 35 and the length of first span 37 may differ from the dimensions and ranges given above. Further, the second span 15 is depicted as having a width of second span 41 and a length of second span 43. In certain embodiments, the width of second span 37 may be about five to about 100 millimeters and the length of second span 43 may be about one to about five centimeters, with a preferable length of, for example, about two to about four centimeters in certain embodiments. The width of second span 37 and the length of second span 43 may be less than or greater than as listed. In certain embodiments, the width of second span 37 may be about one to about 300 millimeters and the length of second span 43 may be about a half to about 30 centimeter centimeters (or may be less than or greater than as desired or required). However, the provided dimensions for both the width of the second span 41 and the length of second span 43 are exemplary and not limiting. It should be appreciated that these dimensions may vary considerably based upon the anatomical, environmental, and structural demands and operational requirements. As with the dimensions provided for the first span 13, both the width of second span 41 and the length of second span 43 may vary based on, for example, an individual patient's anatomy or the targeted anatomical region. That is, when a certain embodiment of the fixation device 11 is used, for example, to stability the syndesmosis of the tibia and fibula, the width of second span 41 and the length of second span 43 may differ from the dimensions and ranges given above. The width of first span 35 and width of second span 37 allows the forces stabilizing the bones to be distributed over a wider surface area so as to further reduce the risk of complications and re-injury. The length of first span 37 and length of second span 43 are sufficiently long to allow the first span 13 and second span 15 to form a closed loop 29 around two anatomic structures so as to fix the anatomic structures in a tensioned state. That is, the ranges provided above would allow a practitioner to form a closed loop 29 around, for example, a coracoid 27 and a clavicle 25 to fix the two bones in a tensioned state in order to treat a severe acromioclavicular injury, as depicted in FIG. 5. However, it would be within the skill of a practitioner to adjust the length of first span 13 and the length of second span 15 to meet the demands of a given application of the fixation device 11. Identification of the appropriate lengths to be used may be determined by observation and experimentation.

The term "about," as used herein, means approximately, in the region of, roughly, or around. When the term "about" is used in conjunction with a numerical range, it modifies that range by extending the boundaries above and below the numerical values set forth. In general, the term "about" is used herein to modify a numerical value above and below the stated value by a variance of 10%. In one aspect, the term "about" means plus or minus 10% of the numerical value of the number with which it is being used. Therefore, about 50% means in the range of 45%-55%. Numerical ranges recited herein by endpoints include all numbers and fractions subsumed within that range (e.g. 1 to 5 includes 1, 1.5, 2, 2.75, 3, 3.90, 4, 4.24, and 5). It is also to be understood that all numbers and fractions thereof are presumed to be modified by the term "about."

In FIG. 6, the securement means are depicted as apertures 18. Each aperture 18 is depicted as having an outer rim, further comprising a specified width of rim 33. In certain embodiments, the width of rim 33 may be about three to about five millimeters.

Further in FIG. 6, the securement means are depicted as a plurality of apertures 18 linearly extending away from the proximal portion of the first span 13 in a sequential fashion. However, it should be appreciated that the precise number of apertures 18 (as well as securement means) as depicted in FIG. 6 is provided for exemplary purposes only. Any number of securement means (e.g., apertures) may comprise the plurality of said securement means (e.g., apertures) extending linearly in a sequential fashion away from the proximal portion of the first span 13. Further, though FIG. 6 depicts the securement means 17 as apertures, this is not meant to be necessary nor limiting and the securement means 17 may take any suitable structural form such as, for example, recesses, grooves, sockets, notches, holes, orifices, slits, slots, ducts, cavities, or other suitable equivalents thereof.

Each aperture 18 in the sequence of securement means is separated by a separation between securement means to define the corresponding separation 31. In certain embodiments, the separation between securement means 31 may be about one centimeter.

FIG. 6 also illustrates a receiving aperture 21 having a diameter of receiving aperture 39. In certain embodiments, the diameter of receiving aperture 39 may be about fifteen to about twenty millimeters.

The fixation device 11 as shown and depicted in FIGS. 1-6 may be constructed of a number of suitable materials. Such materials may include, for example, suture tape, ribbon, plastic, thermoplastic, silicon, braided-high strength polyester suture material, or a collagen tape material. Other materials would also be suitable. Identification of equivalents is well within the skill of the ordinary practitioner and would require no more than routine experimentation. It should be appreciated that the fixation device 11 may be composed of such materials in part or in whole.

Any of the components or modules referred to with regards to any of the present invention embodiments of the device discussed herein, may be integrally or separately formed with one another. Further, redundant functions or structures of the components or modules may be implemented.

Any of the components or modules may be a variety of widths and lengths as desired or required for operational purposes.

It should be appreciated that various sizes, dimensions, contours, rigidity, shapes, flexibility and materials of any of the components or portions of components in the various embodiments of the device discussed throughout may be varied and utilized as desired or required. Similarly, locations and alignments of the various components may vary as desired or required. Moreover, modes and mechanisms for connectivity or interchangeability may vary.

It should be appreciated that the device (and system) and related components of the device (and system) discussed herein may take on all shapes along the entire continual geometric spectrum of manipulation of x, y, and z planes to provide and meet the anatomical, environmental, and structural demands and operational requirements. Moreover, locations and alignments of the various components may vary as desired or required.

It should be appreciated that as discussed herein, a subject may be a human or any animal. It should be appreciated that an animal may be a variety of any applicable type, including, but not limited thereto, mammal, veterinarian animal, livestock animal or pet type animal, etc. As an example, the animal may be a laboratory animal specifically selected to have certain characteristics similar to human (e.g. rat, dog, pig, monkey), etc. It should be appreciated that the subject may be any applicable human patient, for example.

Further, it should be appreciated that an embodiment may be implemented and directed at other target areas or intended areas in addition to those disclosed and discussed. Those of ordinary skill in the art will appreciate that the present invention has a broad application in the field of orthopedic surgery and may be utilized in any setting involving a reduction of separation of subsequent securement of two anatomic structures. For example, an embodiment of the present invention may be utilized in order to stabilize the syndesmosis of the tibia and fibula or to reduce and fix a split sternum.

Of course, it should be understood that a wide range of changes and modifications may be made to the preferred embodiment described above. It is therefore intended that the foregoing detailed description be regarded as illustrative rather than limiting, and that it be understood that it is the following claims, including all equivalents, which are intended to define the scope of this invention.

EXAMPLES

Practice of an aspect of an embodiment (or embodiments) of the invention will be still more fully understood from the following examples and experimental results, which are presented herein for illustration only and should not be construed as limiting the invention in any way.

Example 1. An aspect of an embodiment of the present invention provides, but not limited thereto, an adjustable fixation device for secure fixation of at least a first anatomic structure and a second anatomic structure of a subject. The fixation device may comprise: a first span having a proximal portion and a distal portion opposite said proximal portion; said proximal portion of said first span comprising at least one securement means and said distal portion of said first span comprising a reception aperture; a second span in communication with said first span, said second span comprising at least one attachment means disposed on said second span; wherein said reception aperture is configured to receive said first span and said second span such that said first span and said second span form a first closed loop around said first anatomic structure; wherein said first span and said second span are further configured to extend around said second anatomic structure of said subject; and wherein said at least one securement means is further configured to attach to said attachment means, forming a second closed loop around said first anatomic structure and said second anatomic structure, and fixedly securing said first anatomic structure and said second anatomic structure in a tensioned state.

Example 2. The fixation device in example 1 or 31, wherein said proximal portion of said first span further comprises a plurality of securement means extending linearly in a sequential fashion away from said proximal portion of said first span.

Example 3. The fixation device in example 1 or 31 (as well as subject matter in whole or in part of example 2), wherein said at least one securement means is an aperture configured to receive and engage said attachment means.

Example 4. The fixation device in example 1 or 31 (as well as subject matter of one or more of any combination of examples 2-3, in whole or in part), wherein said at least one securement means is a recess configured to receive and attach to said attachment means.

Example 5. The fixation device in example 1 or 31 (as well as subject matter of one or more of any combination of examples 2-4, in whole or in part), wherein said at least on securement means is a groove configured to receive and attach to said attachment means.

Example 6. The fixation device in example 1 or 31 (as well as subject matter of one or more of any combination of examples 2-5, in whole or in part), wherein said at least one securement means is a socket configured to receive and attach to said attachment means.

Example 7. The fixation device in example 1 or 31 (as well as subject matter of one or more of any combination of examples 2-6, in whole or in part), wherein said attachment means is a protrusion configured to engage and attach to said securement means.

Example 8. The fixation device in example 1 or 31 (as well as subject matter of one or more of any combination of examples 2-7, in whole or in part), wherein said attachment means is a tab configured to engage and attach to said securement means.

Example 9. The fixation device in example 1 or 31 (as well as subject matter of one or more of any combination of examples 2-8, in whole or in part), wherein said device is composed of a material selected from the group consisting of suture tape, ribbon, plastic, thermoplastic, and silicon.

Example 10. The fixation device in example 1 or 31 (as well as subject matter of one or more of any combination of examples 2-9, in whole or in part), wherein said device is composed of a braided high-strength polyester suture material.

Example 11. The fixation device in example 1 or 31 (as well as subject matter of one or more of any combination of examples 2-10, in whole or in part), wherein said device is composed of a collagen tape material.

Example 12. The fixation device in example 1 or 31 (as well as subject matter of one or more of any combination of examples 2-11, in whole or in part), wherein said device is configured to secure an acromioclavicular joint of the subject.

Example 13. The fixation device in example 1 or 31 (as well as subject matter of one or more of any combination of examples 2-12, in whole or in part), wherein said first anatomic structure is a coracoid of the subject and said second anatomic structure is a clavicle of the subject.

Example 14. The fixation device in example 13 (as well as subject matter of one or more of any combination of examples 2-12, in whole or in part), wherein said device is further configured to secure a third anatomic structure of a subject, said third structure being an acromion of the subject.

Example 15. The fixation device in example 1 or 31 (as well as subject matter of one or more of any combination of examples 2-14, in whole or in part), wherein said first anatomic structure is a first portion of a split sternum and said second anatomic structure is a second portion of a split sternum of the subject.

Example 16. The fixation device in example 1 or 31 (as well as subject matter of one or more of any combination of examples 2-15, in whole or in part), wherein said first anatomic structure is a tibia of a human being and said second anatomic structure is a fibula of a human being.

Example 17. The fixation device in example 1 or 31 (as well as subject matter of one or more of any combination of examples 2-16, in whole or in part), further comprising a passing device provided together in a kit.

Example 18. The kit of example 17 (as well as subject matter of one or more of any combination of examples 2-16, in whole or in part), wherein said passing device is configured to advance said fixation device so as to traverse adjacent to said first anatomic structure of said subject.

Example 19. An aspect of an embodiment of the present invention provides, but not limited thereto, a method for securing a joint of a subject. The method may comprise: advancing a fixation device so as to traverse adjacent to a first bone; passing a first span and a second span of said fixation device through a receiving aperture of said device, said receiving aperture being disposed on a proximal portion of said first span of said fixation device, in order to form a first closed loop around said first bone; reducing the separation between said first bone and a second bone; advancing said first span and said second span of said fixation device so as to collectively extend around said second bone; overlapping said first span and said second span to an appropriate degree such that said first bone and said second bone will be secured in a tensioned state; and affixing an attachment means disposed on said second span of said device to a securement means disposed on a distal portion of said first span of said device in order to form a second closed loop around said first bone and said second bone and secure said first bone and said second bone in said tensioned state.

Example 20. The method of example 19, wherein said reduction is provided by said degree of overlap of said first span and said second span so as to reduce the separation.

Example 21. The method of example 19 (as well as subject matter in whole or in part of example 20), wherein said reduction is provided by applying a force to one or both of said first bone and second bone so as to reduce the separation.

Example 22. The method of example 19 (as well as subject matter of one or more of any combination of examples 20-21, in whole or in part), further comprising: providing a passing device to form a kit.

Example 23. The method of example 22 (as well as subject matter of one or more of any combination of examples 20-21, in whole or in part), wherein said fixation device is traversed adjacent to said first bone by: inserting said passing device adjacent said first bone; and utilizing said passing device to advance said fixation device so as to traverse adjacent to said first bone.

Example 24. An aspect of an embodiment of the present invention provides, but not limited thereto, a method for securing a joint of a subject. The method may comprise: inserting a passing device into a space adjacent to a first bone so as to traverse a first bone; utilizing said passing device to advance a fixation device so as to traverse said fixation device adjacent to said first bone; passing a first span and a second span of said fixation device through a receiving aperture of said device, said receiving aperture being disposed on a proximal portion of said first span of said fixation device, in order to form a first closed loop around said first bone; reducing the separation between said first bone and a second bone; advancing said first span and said second span of said fixation device so as to collectively extend around said second bone; overlapping said first span and said second span to an appropriate degree such that said first bone and said second bone will be secured in a tensioned state; and affixing an attachment means disposed on said second span of said device to a securement means disposed on a distal portion of said first span of said device in order to form a second closed loop around said first bone and said second bone and secure said first bone and said second bone in said tensioned state.

Example 25. The method of example 24, wherein said reduction is provided by said degree of overlap of said first span and said second span so as to reduce the separation.

Example 26. The method of example 24 (as well as subject matter in whole or in part of example 25), wherein said reduction is provided by applying a force to one or both of said first bone and second bone so as to reduce the separation.

Example 27. The method of providing instructions to use or operate of any of the devices, systems, assemblies, or their components provided in any one or more of examples 1-26 and 31-32.

Example 28. The method of manufacturing any of the devices, systems, assemblies, or their components provided in any one or more of examples 1-26 and 31-32.

Example 29. It is noted that the machine readable medium or computer useable medium may be configured to execute the subject matter pertaining to system or related methods disclosed in examples 1-26, as well as Examples 27-28 and 31-32.

Example 30. Subject matter of one or more of any combination of examples 1-28 and 31-32 in whole or in part whereby the self-locking and adjustable device that secures and stabilizes two anatomical structures without the use of additional tools to lock the device or bone tunneling techniques to secure the device.

Example 31. An aspect of an embodiment of the present invention provides, but not limited thereto, an adjustable fixation device for securing at least a first intracorporeal anatomic structure and a second intracorporeal anatomic structure of a subject in a fixed tension state, which otherwise would separate away from one another, said fixation device. The fixation device may comprise: a first span having a proximal portion and a distal portion opposite said proximal portion; said proximal portion of said first span comprising at least one securement means and said distal portion of said first span comprising a reception aperture; a second span integrally formed with said first span wherein said second span extends from said first span at a point on a) said reception aperture or b) said first span between said reception aperture and said at least one securement means such that said second span is offset from said first span at a preformed non-zero angle, said second span comprising at least one attachment means disposed on said second span; wherein said reception aperture is configured to receive said proximal portion of said first span and said second span such that said first span and said second span each form a first closed loop entirely around and exterior to said first intracorporeal anatomic structure without attaching said at least one securement means with said attachment means; and wherein said first span and said second span are further configured to extend around and exterior to said second intracorporeal anatomic structure of said subject. Further, said at least one securement means comprises a plurality of securement means extending linearly in a sequential fashion along said proximal portion of said first span; and wherein said at least one of said plurality of securement means is further configured to attach to said attachment means, forming: a second closed loop around said first intracorporeal anatomic structure and said second intracorporeal anatomic structure, and fixedly securing said first intracorporeal anatomic structure and said second intracorporeal anatomic structure in a tensioned state at a specified distance from one another; and wherein length of said second close loop is adjustable as being dependent on the specific said one of plurality of securement means that is attached to said attachment means.

Example 32. The fixation device in example 31, wherein said plurality of securement means is manually detachable from said attachment means without any additional hardware or mechanisms, and whereby after being detached any of said specific said one of plurality of securement means may be selected for reattachment to said attachment means.

REFERENCES

The devices, systems, apparatuses, materials, compositions, components, computer readable medium, algorithms, and methods (of manufacture and use) of various embodiments of the invention disclosed herein may utilize aspects disclosed in the following references, applications, publications and patents and which are hereby incorporated by reference herein in their entirety (and which are not admitted to be prior art with respect to the present invention by inclusion in this section):
1. U.S. Pat. No. 5,766,218, Arnott, R., "Surgical Binding Device and Method of Using Same", Jun. 16, 1998.
2. U.S. Pat. No. 5,964,765, Fenton, Jr., et al., "Soft Tissue Fixation Device", Oct. 12, 1999.
3. U.S. Pat. No. 8,740,913 B2, Schneider, D., "Apparatus and Method for Arthroscopic Transhumeral Rotator Cuff Repair", Jun. 3, 2014.
4. International Patent Application Publication No. WO 2016/154550 A1, Golden, et al., "Joint Repair System", Sep. 29, 2016.
5. Baldwin, K., et al., "Luggage Tag Technique of Anatomic Fixation of Displaced Acromioclavicular Joint Separations", Clinical Orthopaedics and Related Research (2010), 468: 259-265.
6. U.S. Pat. No. 8,512,376 B2, Thornes, B., "Method and Apparatus for Internal Fixation of an Acromiclavicular Joint Dislocation of the Shoulder", Aug. 20, 2013.
7. U.S. Pat. No. 8,162,997 B2, Struhl, S., "Device for Treatment of Acromioclavicular Joint Dislocations", Apr. 24, 2012.
8. U.S. Pat. No. 9,332,979 B2, Sullivan, et al., "Tensionable Knotless Acromiclavicular Repairs and Constructs", May 10, 2016.
9. Turman K A, Miller C D, Miller M D, "Clavicular fractures following coracoclavicular ligament reconstruction with tendon graft: a report of three cases", J Bone Joint Surg. 2010; 92(6):1526-32.
10. Milewski M D, Tompkins M A, Guigale J M, Carson E W, Miller M D, Diduch D R. Complications Related to Anatomic Reconstruction of the Coracoclavicular Ligaments", Am. J. Sports Med., 2012; 40: 1628-1634.
11. U.S. Pat. No. 5,409,490, Ethridge, J., "Shoulder Separation Reconstruction", Apr. 25, 1995.
12. U.S. Pat. No. 5,645,588, Graf et. al., "Graft Attachment Device", Jul. 8, 1997.
13. U.S. Pat. No. 9,387,011 B2, Chudik, S., "Acromioclavicular Joint Repair System," Jul. 12, 2016.
14. Mohamed Taha El Shewy, et al., "Suture Repair Using Loop Technique in Cases of Acute Complete Acrmioclavicular Joint Dislocation", Journal of Ortopaed Traumatol (2011), 12:29-35.

Unless clearly specified to the contrary, there is no requirement for any particular described or illustrated activity or element, any particular sequence or such activities, any particular size, speed, material, duration, contour, dimension or frequency, or any particularly interrelationship of such elements. Moreover, any activity can be repeated, any activity can be performed by multiple entities, and/or any element can be duplicated. Further, any activity or element can be excluded, the sequence of activities can vary, and/or the interrelationship of elements can vary. It should be appreciated that aspects of the present invention may have a variety of sizes, contours, shapes, compositions and materials as desired or required.

In summary, while the present invention has been described with respect to specific embodiments, many modifications, variations, alterations, substitutions, and equivalents will be apparent to those skilled in the art. The present invention is not to be limited in scope by the specific embodiment described herein. Indeed, various modifications of the present invention, in addition to those described herein, will be apparent to those of skill in the art from the foregoing description and accompanying drawings. Accordingly, the invention is to be considered as limited only by the spirit and scope of the following claims, including all modifications and equivalents.

Still other embodiments will become readily apparent to those skilled in this art from reading the above-recited detailed description and drawings of certain exemplary embodiments. It should be understood that numerous variations, modifications, and additional embodiments are possible, and accordingly, all such variations, modifications, and embodiments are to be regarded as being within the spirit and scope of this application. For example, regardless of the content of any portion (e.g., title, field, background, summary, abstract, drawing figure, etc.) of this application, unless clearly specified to the contrary, there is no requirement for the inclusion in any claim herein or of any application claiming priority hereto of any particular described or illustrated activity or element, any particular sequence of such activities, or any particular interrelationship of such elements. Moreover, any activity can be repeated, any activity can be performed by multiple entities, and/or any element can be duplicated. Further, any activity or element can be excluded, the sequence of activities can vary, and/or the interrelationship of elements can vary. Unless clearly specified to the contrary, there is no requirement for any particular described or illustrated activity or element, any particular sequence or such activities, any particular size, speed, material, dimension or frequency, or any particularly interrelationship of such elements. Accordingly, the descriptions and drawings are to be regarded as illustrative in nature, and not as restrictive. Moreover, when any number or range is described herein, unless clearly stated otherwise, that number or range is approximate. When any range is described herein, unless clearly stated otherwise, that range includes all values therein and all sub ranges therein. Any information in any material (e.g., a United States/foreign patent, United States/foreign patent application, book, article, etc.) that has been incorporated by reference herein, is only incorporated by reference to the extent that no conflict exists between such information and the other statements and drawings set forth herein. In the event of such conflict, including a conflict that would render invalid any claim herein or seeking priority hereto, then any such conflicting information in such incorporated by reference material is specifically not incorporated by reference herein.

I claim:
1. An adjustable fixation device for securing at least a first intracorporeal anatomic structure and a second intracorporeal anatomic structure of a subject in a tensioned state, which otherwise would separate away from one another, said fixation device comprising:
  a first span having a proximal portion and a distal portion opposite said proximal portion;

said proximal portion of said first span comprising a plurality of securement means extending linearly in a sequential fashion along said proximal portion of said first span and said distal portion of said first span comprising a reception aperture;

a second span integrally formed with said first span wherein said second span extends from said first span at a point on a) said reception aperture or b) said first span between said reception aperture and said plurality of securement means such that said second span is offset from said first span at a preformed non-zero angle, said second span comprising at least one attachment means disposed on said second span;

wherein said reception aperture is configured to receive said proximal portion of said first span and said second span such that said first span and said second span each form a first closed loop entirely around and exterior to said first intracorporeal anatomic structure without attaching said plurality of securement means with said at least one attachment means;

wherein said first span and said second span are further configured to extend around and exterior to said second intracorporeal anatomic structure of said subject to form a second closed loop around said first intracorporeal anatomic structure and said second intracorporeal anatomic structure;

wherein at least one of said plurality of securement means is further configured to attach to said at least one attachment means to secure said second closed loop and to fixedly secure said first intracorporeal anatomic structure and said second intracorporeal anatomic structure in a tensioned state at a specified distance from one another;

wherein a length of said second closed loop is adjustable and is dependent on the specific said at least one of said plurality of securement means that is attached to said at least one attachment means; and wherein said second span is offset from said first span at said preformed non-zero angle before said first and second closed loops are formed.

2. The fixation device in claim 1, wherein each of said plurality of securement means is an aperture configured to receive and engage said at least one attachment means.

3. The fixation device in claim 1, wherein each of said plurality of securement means is a recess configured to receive and attach to said at least one attachment means.

4. The fixation device in claim 1, wherein each of said plurality of securement means is a groove configured to receive and attach to said at least one attachment means.

5. The fixation device in claim 1, wherein each of said plurality of securement means is a socket configured to receive and attach to said at least one attachment means.

6. The fixation device in claim 1, wherein said at least one attachment means is a protrusion configured to engage and attach to one of said plurality of securement means.

7. The fixation device in claim 1, wherein said at least one attachment means is a tab configured to engage and attach to one of said plurality of securement means.

8. The fixation device in claim 1, wherein said device is composed of a material selected from the group consisting of suture tape, ribbon, plastic, thermoplastic, and silicon.

9. The fixation device in claim 1, wherein said device is composed of a braided high-strength polyester suture material.

10. The fixation device in claim 1, wherein said device is composed of a collagen tape material.

11. The fixation device in claim 1, wherein said device is configured to secure an acromioclavicular joint of the subject.

12. The fixation device in claim 1, wherein said first intracorporeal anatomic structure is a coracoid of the subject and said second intracorporeal anatomic structure is a clavicle of the subject.

13. The fixation device in claim 1, wherein said at least one of said plurality of securement means is manually detachable from said at least one attachment means without any additional hardware or mechanisms, and whereby after being detached any of said plurality of securement means may be selected for reattachment to said at least one attachment means.

* * * * *